United States Patent [19]

Ehrenfreund

[11] 4,353,925
[45] Oct. 12, 1982

[54] INSECTICIDAL N-[4-(3'-HALOPROP-2'-EN-1'-YL)-AMINO-PHENYL]-N'-BENZOYLUREAS

[75] Inventor: Josef Ehrenfreund, Allschwil, Switzerland

[73] Assignee: Ciba-Geigy Corporation, Ardsley, N.Y.

[21] Appl. No.: 281,546

[22] Filed: Jul. 9, 1981

[30] Foreign Application Priority Data

Jul. 16, 1980 [CH] Switzerland .................. 5457/80
Aug. 12, 1980 [CH] Switzerland .................. 6095/80
Feb. 26, 1981 [CH] Switzerland .................. 1294/81
Jun. 3, 1981 [CH] Switzerland .................. 3628/81

[51] Int. Cl.³ .................. A01N 47/34; C07C 127/22
[52] U.S. Cl. .................. 424/322; 564/44
[58] Field of Search .................. 564/44; 424/322

[56] References Cited

U.S. PATENT DOCUMENTS

Re. 30,563 3/1981 Abdulla et al. .................. 564/44
3,933,908 1/1976 Wellinga et al. .................. 564/44

FOREIGN PATENT DOCUMENTS 16729 10/1980 European Pat. Off. .............. 564/44

OTHER PUBLICATIONS

Wellinga et al., J. Agr. Food Chem., vol. 21, No. 3, (1973) pp. 348-354.

Primary Examiner—John F. Terapane
Assistant Examiner—Frederick W. Pepper
Attorney, Agent, or Firm—Frederick H. Rabin

[57] ABSTRACT

Novel substituted N-(p-aminophenyl)-N'-benzoylureas of the formula I

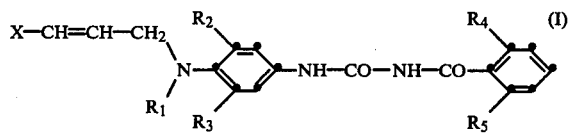

wherein $R_1$ is hydrogen, $C_1$-$C_4$-alkyl, $C_3$-alkenyl, $C_3$-alkenyl substituted by a chlorine or bromine atom, or $R_1$ is $C_3$-$C_6$-cycloalkyl, $R_2$ and $R_3$ are each hydrogen or halogen, $R_4$ is methyl or halogen, $R_5$ is hydrogen or halogen, and X is chlorine or bromine, the salts of these compounds, processes for producing these compounds, as well as compositions containing them, for use in combating pests, particularly for combating insects which infest plants and animals. The novel compounds are especially effective against larval stages and eggs of insects which damage plants by eating.

14 Claims, No Drawings

INSECTICIDAL N-[4-(3'-HALOPROP-2'-EN-1'-YL)-AMINO-PHENYL]-N'-BENZOYLUREAS

The present invention relates to novel substituted N-(p-aminophenyl)-N'-benzoylureas, to processes for producing them, and to their use in combating pests.

The substituted N-(p-aminophenyl)-N'-benzoylureas according to the invention have the formula I

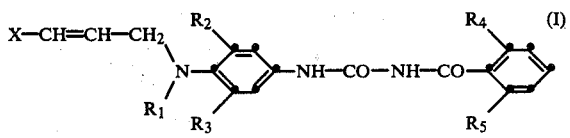

wherein $R_1$ is hydrogen, $C_1$-$C_4$-alkyl, $C_3$-alkenyl, $C_3$-alkenyl substituted by a chlorine or bromine atom, or $R_1$ is $C_3$-$C_6$-cycloalkyl, $R_2$ and $R_3$ are hydrogen or halogen, $R_4$ is methyl or halogen, $R_5$ is hydrogen or halogen, and X is chlorine or bromine.

The present invention relates also to the salts of the compounds of the formula I, that is, the salts which are suitable from an agricultural standpoint and with regard to tolerance to plants. Examples of acids suitable for forming salts are: hydrochloric acids, such as HCl, HBr, HJ, phosphoric acid, perchloric acid, thiocyanic acid, tetrafluoroboric acid, nitric acid, sulfuric acid, aliphatic and aromatic sulfonic acids, fatty acids, trichloro- and trifluoroacetic acid and also polyvalent organic acids, such as oxalic acid, malonic acid, succinic acid, tartaric acid, adipic acid and citric acid.

Examples of alkyl groups covered by the definition $C_1$-$C_4$-alkyl according to the invention are: methyl, ethyl, n-propyl, i-propyl as well as the four isomeric butyl groups. And by halogen is meant, within the scope of the invention: fluorine, chlorine, bromine and iodine, preferably fluorine, chlorine and bromine.

The compounds of the formula I occur generally as cis/trans isomeric mixtures. The term 'compounds of the formula I' is thus to be understood as embracing both the cis and trans forms and the corresponding isomeric mixtures or isomeric combinations. An isomeric mixture can be separated for example by means of known chromatographical methods of separation into the isomeric forms. In certain cases, the isomeric separation can be effected by fractional crystallisation.

Compounds of the formula I preferred on account of their action as pesticidal active substances are those wherein $R_1$ is $C_1$-$C_4$-alkyl, $CH_2$=CH—$CH_2$-, Cl—CH=CH—$CH_2$—, Br—CH=CH—$CH_2$ or cyclopropyl; $R_2$ and $R_3$ are each chlorine or bromine; $R_4$ is fluorine, chlorine, bromine or methyl; and $R_5$ is hydrogen, fluorine or chlorine. Of importance are additionally those compounds of the formula I wherein $R_1$ is $C_1$-$C_4$-alkyl; $R_2$ and $R_3$ are each chlorine or bromine; $R_4$ is fluorine or chlorine; and $R_5$ is hydrogen, fluorine or chlorine. To be emphasised also are the compounds of the formula I wherein $R_2$ and $R_3$ are each chlorine. Further valuable compounds of the formula I by virtue of their biological activity are those wherein $R_1$ is methyl; as well as those wherein $R_4$ and $R_5$ are fluorine or chlorine; and those wherein $R_4$ and $R_5$ are fluorine.

The compounds of the formula I can be produced by processes known per se (cp., inter alia, the German Offenlegungsschriften Nos. 2,123,236 and 2,601,780, and the European Patent Application No. 13 414).

A compound of the formula I can thus be obtained for example (a) by reaction of a compound of the formula II

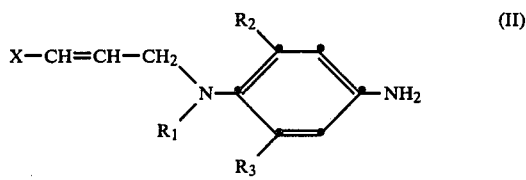

with a compound of the formula III

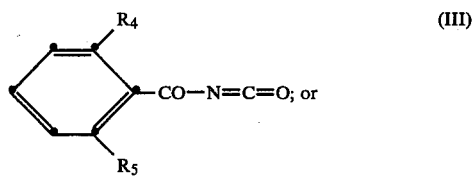

(b) by reaction of a compound of the formula IV

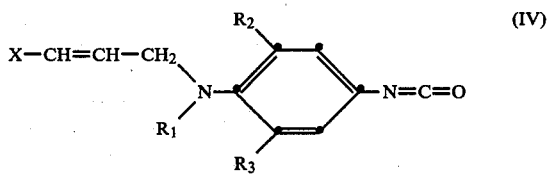

with a compound of the formula V

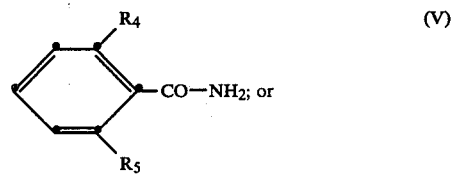

(c) by reaction of a compound of the formula II with a compound of the formula VI

In the above formulae II, III, IV, V and VI, the symbols $R_1$, $R_2$, $R_3$, $R_4$, $R_5$ and X have the meanings defined under the formula I, and R is a lower or medium $C_1$-$C_8$-alkyl group which is unsubstituted or substituted by halogen.

The processes (a) to (c) mentioned are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chlorine, carbon tetrachloride and chlorobenzene; nitriles, such as acetonitrile or propionitrile; dimethyl sulfoxide, as well as ketones, for example acetone, methyl ethyl ketone, methyl-isopropyl ketone and methyl-isobutyl ketone. Process (a) is in general performed at a temperature of −10° to 100° C., preferably between 15° and 25° C., optionally in the presence of an organic base, for example triethylamine. Process (b) is carried out at a temperature of 0° to 150° C., preferably at the boiling point of the employed solvent, and optionally in the presence of an organic base, such as pyridine, and/or with the addition of an alkali metal or alkaline-earth metal, preferably sodium. For the reaction of the urethanes VI according to process (c), the temperatures chosen are between 60° C. and the boiling point of the reaction mixture. Suitable solvents are above all aromatic hydrocarbons, such as toluene, xylene, chlorobenzene, and so forth.

The salts of the compounds of the formula I are produced by procedures generally known.

The starting materials of the formulae II, III, IV, V and VI given in the foregoing are known, or in cases where they are new they can be produced by processes analogous to known processes. Thus, for example, the p-phenylenediamines of the formula II can be produced by N-halo-alkenylation and, optionally, N-alkylation of the corresponding p-nitroanilines, with subsequent chemical reduction (for example with iron in aqueous acids) of the nitro group to the amino group. A further possibility for producing the p-phenylenediamines of the formula II is to react the p-halonitrobenzene of the formula VII

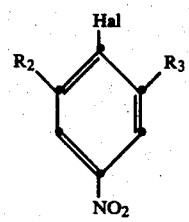

with a secondary amine of the formula VIII

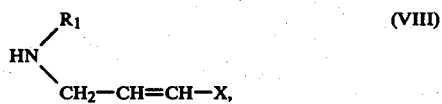

and to subsequently reduce the nitro group in the manner stated above, $R_1$, $R_2$ and $R_3$ having the meanings defined in the foregoing, and "Hal" being a halogen atom, preferably chlorine or bromine. The isocyanates of the formula IV are obtainable by reacting the corresponding N,N-substituted p-phenylenediamines of the formula II (or the hydrochlorides thereof) with phosgene, using in general customary processes. The compounds of the formula III can be obtained as follows (cp. J. Agr. Food Chem. 21(3), pp. 348 and 993; 1973):

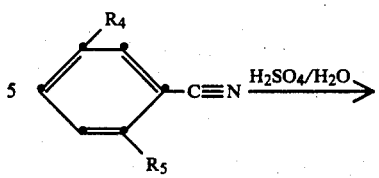

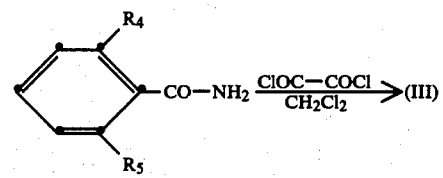

In the above formulae, $R_4$ and $R_5$ have the meanings given under the formula I. The compounds of the formula VI are produced by reaction of the benzamides X with corresponding chloroformic acid esters.

It is already known that specific N-phenyl-N'-benzoylureas have insecticidal properties (cp. German Offenlegungsschriften Nos. 2,123,236, 2,504,982, 2,537,413, 2,601,780 and 2,726,684, the Belgian Pat. Nos. 832,304, 843,906, 844,066 and 867,046, and also the U.S. Pat. No. 4,089,975). The German Offenlegungsschrift No. 2,926,480 relates to substituted N-(p-alkylenephenylamino)-phenyl-N'-benzylureas and -thioureas having insecticidal activity. Furthermore, there are known from J. Agr. Food Chem. 21, No. 3, 348 ff, (1973) substituted N-phenyl-N'-2,6-dichlorobenzoylureas which are said to have insecticidal properties. On page 353 of this publication are mentioned corresponding N-(4-dimethylamino)phenyl derivatives and N-(3-chloro-4-dimethylamino)-phenyl derivatives, which however, as can be seen from the Table III given therein—have inadequate insecticidal action.

It has now been found that surprisingly, compared with the above compounds, the compounds of the formula I according to the invention, whilst having high tolerance to plants and negligible toxicity to warm-blooded animals, exhibit an excellent degree of effectiveness as pesticidal active substances. They are suitable in particular for combating pests which infest plants and animals.

The compounds of the formula I and the compositions containing them are especially suitable for combating insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Besides having a very favourable action against flies, for example *Musca domestica*, and against mosquito larvae, the compounds of the formula I and the compositions containing them are suitable also for combating insects which damage plants by eating, in crops of ornamental plants and productive plants, especially in cotton crops (for example against *Spodoptera littoralis* and *Heliothis virescens*), and also in fruit and vegetable crops (for example against *Leptinotarsa decemlineata*, *Pieris brassicae* and *Laspeyresia pomonella*). To be emphasised in particular is the ovicidal and larvicidal action of compounds of the formula I. When compounds of the formula I are taken up with the feed by adult insects, there is observed in many cases, especially with Coleoptera, for example *Anthonomus grandis*, a reduced oviposition and/or a lessened rate of hatching.

The compounds of the formula I and the compositions containing them are moreover suitable for combating ectoparasites, especially ectoparasitic insects, such as *Lucilia sericata*, in both domestic and productive animals, for example by treatment of animals, livestock housing and pasture land.

The action of the compounds according to the invention or of the compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, pyrethroids, carbamates, chlorinated hydrocarbons and *Bacillus thuringiensis* preparations.

It has been shown that preparations which contain the compounds of the formula I according to the invention together with the known insecticide "Galecron" [$N^2$-(4-chloro-2-methyl-phenyl)-$N^1$,$N^1$-dimethyl-formamidine] are distinguished by a surprisingly high insecticidal activity and a particularly wide spectrum of application.

The compounds of the formula I can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I or the salts thereof are used as such or preferably together with auxiliaries common in formulation practice: they can be processed for example, in a manner known per se, into the form of emulsion concentrates, directly sprayable or dilutable solutions, diluted emulsions, wettable powders, soluble powders, dusts or granulates, and also encapsulations, for example in polymeric substances. The method of application, such as spraying, atomising, dusting, scattering or pouring, is selected—as is the type of composition—according to the objectives to be achieved and the given circumstances.

The formulations, that is to say, the compositions containing the active substance of the formula I and optionally a solid or liquid additive, are produced in a known manner, for example by the intimate mixing and/or grinding of the active substances with extenders, such as with solvents, solid carriers and, if required, with surface-active compounds (tensides).

Suitable solvents are: aromatic hydrocarbons, preferably the fractions $C_8$ to $C_{12}$, for example xylene mixtures or substituted naphthalenes, phthalic acid esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl ether or -ethyl ether, ketones, such as cyclohexanone, strongly polar solvents, such as N-methyl-2-pyrrolidone, dimethylsulfoxide or dimethylformamide, and also optionally epoxidised vegetable oils, such as epoxidised coconut oil or soyabean oil; or water.

The solid carriers used, for example for dusts and dispersible powders, are as a rule natural mineral fillers, such as calcite, talcum, kaolin, montmorillonite or attapulgite. In order to improve the physical properties, it is possible to use also highly dispersed silicic acid or highly dispersed absorbent polymers. Suitable granulated adsorptive carriers are porous types, for example pumice, ground brick, sepiolite or bentonite; and suitable nonsorbent carriers are for example calcite and sand. There can also be used a great number of pregranulated materials of inorganic or organic nature, such as in particular dolomite or ground plant residues.

Suitable surface-active compounds are, depending on the nature of the active substance of the formula I to be formulated, nonionic, cation-active and/or anion-active tensides having good emulsifying, dispersing and wetting properties. By tensides are also meant mixtures of tensides.

Suitable anionic tensides can be both so-called water-soluble soaps and water-soluble synthetic, surface-active compounds. Soaps which are suitable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts. More frequently used however are so-called synthetic tensides, especially fatty sulfonates, fatty sulfates, sulfonated benzimidazole derivatives or alkylaryl sulfonates. The fatty sulfonates or fatty sulfates are as a rule in the form of alkali metal, alkaline-earth metal or optionally substituted ammonium salts, and contain an alkyl group having 8 to 22 C atoms, alkyl also including the alkyl moiety of acyl radicals, for example the Na or Ca salt of ligninsulfonic acid, of dodecylsulfuric acid ester or of a fatty alcohol sulfate mixture produced from natural fatty acids. To these belong also the salts of sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Alkylaryl sulfonates are for example the Na, Ca or triethanolamine salts of dodecylbenzenesulfonic acid, of dibutylnaphthalenesulfonic acid or of a naphthalenesulfonic acid/formaldehyde condensation product. Suitable also are corresponding phosphates, for example salts of the phosphoric acid ester of a p-nonylphenol-(4-14)-ethylene oxide adduct. Nonionic tensides which can be used are in particular polyglycol ether derivatives of aliphatic or cycloaliphatic alcohols, of saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Further suitable nonionic tensides are the water-soluble polyethylene oxide adducts (which contain 20 to 250 ethylene glycol ether groups and 10 to 100 propylene glycol ether groups) with polypropylene glycol, ethylenediaminopolypropylene glycol and alkylpolypropylene glycol having 1 to 10 carbon atoms in the alkyl chain. The stated compounds usually contain 1 to 5 ethylene glycol units per propylene glycol unit. Examples of nonionic tensides which may be mentioned are: nonylphenolpolyethoxyethanols, castor oil polyglycol ethers, polypropylene-/polyethyleneoxy adducts, tributylphenoxypolyethoxyethanol, polyethylene glycol and octylphenoxypolyethoxyethanol. Also applicable are fatty acid esters of polyoxyethylenesorbitan, such as polyoxyethylenesorbitan-trioleate. In the case of the cationic tensides, they are in particular quaternary ammonium salts which contain as N-substituents at least one alkyl group having 8 to 22 C atoms, and, as further substituents, lower, optionally halogenated alkyl, benzyl or lower hydroxyalkyl radicals. The salts are preferably in the form of halides, methyl sulfates or ethyl sulfates, for example stearyl-trimethylammonium chloride or benzyldi(2-chloroethyl)ethylammonium bromide.

The tensides commonly used in formulation practice are described in, iner alia, the following publications:
"Mc Cutcheon's Detergents and Emulsifiers Annual" MC Publishing Corp., Ringwood, N.J., 1979.
Sisely and Wood, "Encyclopedia of Surface Active Agents", Chemical Publishing Co., Inc. New York.

The pesticidal preparations contain as a rule 0.01 to 99%, especially 0.1 to 95%, of active substance of the formula I, 1 to 99% of a solid or liquid additive, and 0 to 25%, particularly 0.1 to 25%, of a tenside.

Whereas concentrated preparations are preferred as commercial products, the end consumer generally uses diluted preparations.

The preparations can also contain further additives, such as stabilisers, antifoam agents, viscosity regulators, binders, adhesives and also fertilisers or other active substances to obtain special effects.

FORMULATION EXAMPLES FOR ACTIVE SUBSTANCES OF THE FORMULA I
(% = PERCENT BY WEIGHT)

| 1. Wettable powders | (a) | (b) |
| --- | --- | --- |
| active substance | 20% | 60% |
| Na—lignin sulfonate | 5% | 5% |
| Na—lauryl sulfate | 3% | — |
| Na—diisobutylnaphthalenesulfonate | — | 6% |
| octylphenolpolyethylene glycol ether (7-8 mols of ethylene oxide) | — | 2% |
| highly dispersed silicic acid | 5% | 27% |
| kaolin | 67% | — |

The active substance is well mixed with the additives and the mixture is thoroughly ground in a suitable mill. There are obtained wettable powders which can be diluted with water to give suspensions of the concentration desired.

| 2. Emulsion concentrate | |
| --- | --- |
| active substance | 10% |
| octylphenolpolyethylene glycol ether (4-5 mols of ethylene oxide) | 3% |
| Ca dodecylbenzenesulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 3. Dusts | (a) | (b) |
| --- | --- | --- |
| active substance | 5% | 8% |
| talcum | 95% | — |
| kaolin | — | 92% |

Dusts ready for use are obtained by mixing the active substance with the carriers, and grinding the mixture in a suitable mill.

| 4. Extruder granulate | |
| --- | --- |
| active substance | 10% |
| sodium lignin sulfonate | 2% |
| carboxymethylcellulose | 1% |
| kaolin | 87% |

The active substance is mixed and ground with the additives, and the mixture is subsequently moistened with water. This mixture is extruded and then dried in a stream of air.

| 5. Coated granulate | |
| --- | --- |
| active substance | 3% |
| polyethylene glycol (MG 200) | 3% |
| kaolin | 94% |

The finely ground active substance is uniformly applied, in a mixer, to the kaolin moistened with polyethylene glycol. Non-dusty coated granulates are obtained in this manner.

| 6. Suspension concentrate | |
| --- | --- |
| active substance | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32.0% |

The finely ground active substance is intimately mixed with the additives. There is thus obtained a suspension concentrate from which can be produced, by dilution with water, suspensions of any concentration desired.

EXAMPLE 1

5.2 g of 3,5-dichloro-4-N-methyl-N-(3-chloroprop-2-en-1-yl)amino-aniline were dissolved in absolute ether, and, with cooling and the exclusion of moisture, 4 g of 2,6-difluorobenzoylisocyanate were added. The precipitate occurring after some time was filtered off with suction and recrystallised from alcohol. The yield was 5.6 g of $N^1$-3,5-dichloro-4-N-methyl-N-(3-chloroprop-2-en-1-yl)amino-phenyl-$N^2$-2,6-difluorobenzoylurea, m.p. 155°–157° C. (compound No. 1).

The following compounds of the formula I are produced in a manner analogous to that described in the foregoing:

| Compound No. | $R_1$ | $R_2$ | $R_3$ | $R_4$ | $R_5$ | X | Melting point [°C.] |
| --- | --- | --- | --- | --- | --- | --- | --- |
| 1 | $CH_3$ | Cl | Cl | F | F | Cl | 155–157 |
| 2 | $CH_3$ | H | H | F | F | Cl | 163–171 |
| 3 | $-(CH_2)_3-CH_3$ | Cl | Cl | F | F | Cl | 115–118 |
| 4 | $-CH_2-CH=CHCl$ | Cl | Cl | F | F | Cl | 160–162 |
| 5 | $-CH(CH_3)_2$ | Cl | Cl | F | F | Cl | 152–154 |
| 6 | $-(CH_2)_3-CH_3$ | Cl | Cl | F | H | Cl | 88–90 |
| 7 | $-CH_2-CH=CH_2$ | Cl | Cl | F | F | Cl | 98–100 |
| 8 | $-CH_3$ | Cl | Cl | Cl | H | Cl | 163–165 |
| 9 | $-CH_3$ | Cl | Cl | F | Cl | Cl | 167–168 |
| 10 | $-CH_3$ | Cl | Cl | F | H | Cl | 163–165 |
| 11 | $-CH_3$ | Cl | Cl | Cl | Cl | Cl | |

-continued

| Compound No. | R₁ | R₂ | R₃ | R₄ | R₅ | X | Melting point [°C] |
|---|---|---|---|---|---|---|---|
| 12 | —CH₃ | Cl | Cl | Br | H | Cl | 169–171 |
| 13 | —CH₃ | Cl | Cl | CH₃ | H | Cl | 153–155 |
| 14 | —CH₃ | Cl | Br | F | F | Cl | 158–159 |
| 15 | —CH₃ | Cl | Br | Cl | H | Cl | 167–169 |
| 16 | —CH₃ | Br | Br | F | F | Cl | |
| 17 | —CH₃ | Br | Br | Cl | H | Cl | |
| 18 | cyclopropyl | Cl | Cl | F | F | Cl | |
| 19 | cyclopropyl | Cl | Cl | Cl | H | Cl | 123–124 |
| 20 | cyclohexyl-H | Cl | Cl | F | F | Cl | |
| 21 | cyclohexyl-H | Cl | Cl | Cl | H | Cl | |
| 22 | —CH₃ | H | H | Cl | H | Cl | |
| 23 | —CH₃ | H | H | F | H | Cl | |
| 24 | —CH₂—CH=CHCl | H | H | F | F | Cl | |
| 25 | H | Cl | Cl | F | F | Cl | |
| 26 | CH₃ | Cl | Cl | F | F | Br | 139–141 |
| 27 | CH₃ | Cl | Cl | Cl | F | Br | 147–148 |
| 28 | CH₃ | Cl | Cl | Cl | H | Br | 149–151 |
| 29 | CH₃ | Cl | Cl | F | H | Br | 151–154 |
| 30 | CH₃ | Cl | Cl | Cl | Cl | Br | |
| 31 | CH₃ | Cl | Cl | CH₃ | H | Br | 145–147 |
| 32 | CH₃ | Br | Cl | F | F | Br | 145–147 |
| 33 | CH₃ | Br | Cl | Cl | H | Br | 155–156,5 |
| 34 | CH₃ | Br | Br | F | F | Br | |
| 35 | CH₃ | Br | Br | Cl | H | Br | |
| 36 | CH₃ | Cl | Cl | Br | H | Br | 159–161 |
| 37 | —CH₂—CH=CHBr | Cl | Cl | F | F | Br | |
| 38 | —CH₂—CH=CHBr | Cl | Cl | Cl | H | Br | |
| 39 | CH₃ | Cl | Br | Cl | F | Br | 159–160 |
| 40 | CH₃ | Cl | Br | F | H | Br | 158–160 |

EXAMPLE 2

Action against *Lucilia sericata*

1 ml of an aqueous preparation containing 0.5% of active substance was added to 9 ml of a culture medium at 50° C. About 30 freshly hatched *Lucilia sericata* maggots were then placed onto the culture medium, and after 48 and 96 hours, respectively, the insecticidal action was determined by ascertaining the mortality rate.

Compounds according to Example 1 exhibited in this test a good action against *Lucilia sericata*.

EXAMPLE 3

Action against *Aedes aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 three-day-old Aëdes larvae were placed into each container. The mortality rate was ascertained after 1, 2 and 5 days.

Compounds according to Example 1 exhibited in this test a good action against *Aedes aegypti*.

EXAMPLE 4

Insecticidal stomach-poison action

Cotton plants were sprayed with aqueous active-substance emulsions (obtained from a 10% emulsifiable concentrate), which contained increasing amounts of the active-substance compound. After drying of the applied coating, larvae of *Spodoptera littoralis* and *Heliothis virescens*, respectively, in the third larval stage were settled onto the cotton plants. The test was carried out at 24° C. with 60% relative humidity. At intervals in each case of 24 hours, an assessment was made of the percentage mortality rate of the test insects and of damage caused by eating.

EXAMPLE 5

Ovicidal action on *Spodoptera littoralis*

Eggs of *Spodoptera littoralis*, not older than 24 hours and deposited on filter paper, were cut out of the paper and immersed in a solution of 400 ppm of the active substance in an acetone/water mixture (1:1), the duration of immersion being one minute. The deposited eggs treated in this manner were then removed from the solution, and placed at 28° C. with 60% relative humidity into plastic dishes. An assessment was made after 5 days of the hatching rate, that is to say, of the number of larvae which had developed from the treated eggs.

Compounds according to Example 1 exhibited in the above test a good action.

EXAMPLE 6

Action on *Laspeyresia pomonella* (eggs)

Deposited *Laspeyresia pomonella* eggs, which were not older than 24 hours, were immersed on filter paper for 1 minute in acetonic-aqueous solutions containing increasing amounts of the active substance to be tested. After drying off the solution, the eggs were transferred to Petri dishes and kept at a temperature of 28° C. The percentage rate of hatching from the treated eggs was determined after 6 days.

EXAMPLE 7

Chemosterilising action on *Anthonomus grandis*

Adult *Anthonomus grandis*, which had been hatched no longer than 24 hours, were transferred, in groups each of 25 beetles, to cages having lattice walls. The cages containing the beetles were then immersed for 5 to 10 seconds in an acetonic solution containing 1.0 percent by weight of the active substance to be tested. After the beetles were again dry, they were placed, for copulation and oviposition, into covered dishes containing feed. Deposited eggs were flushed out with running water two to three times weekly; they were counted, disinfected by being placed for two to three hours in an aqueous disinfectant (such as "Actamer B 100"), and then deposited into dishes containing a suitable larval diet. The eggs were examined after 7 days to determine whether larvae had developed from the deposited eggs.

In order to ascertain the duration of the chemosterilant effect of the active substance tested, the oviposition of the beetles was observed during a period of about four weeks. The evaluation was on the basis of the reduction of the number of eggs laid and larvae hatched in comparison with that in the case of untreated control specimens.

Compounds according to Example 1 exhibited a good action in the above test.

BIOLOGICAL RESULTS

The following Table shows the results of biological test on compounds according to the invention on the basis of the above biological Examples. The criterion used for evaluating the results of the tests was the % mortality rate, the evaluation index being as follows:

A: 80–100% mortality rate at a concentration of 0.75 ppm of the compound tested;
B: 80–100% mortality rate at the concentration of 3.0 ppm of the compound tested;
C: 80–100% mortality rate at a concentration of 12.5 ppm of the compound tested;
D: 80–100% mortality rate at a concentration of 50 ppm of the compound tested;
E: 80–100% mortality rate at a concentration of 100 ppm of the compound tested;
F: 80–100% mortality rate at a concentration of 200 ppm of the compound tested;
G: 80–100% mortality rate at a concentration of 400 ppm of the compound tested;
H: less than 80% mortality rate at a concentration of 800 ppm of the compound tested;

TABLE OF BIOLOGICAL RESULTS

| Compound No | Pesticidal effectiveness | | |
|---|---|---|---|
| | Spodoptera (Example 4) | Heliothis (Example 4) | Laspeyresia (Example 6) |
| 1 | A | C | C |
| 2 | H | H | — |
| 3 | B | D | — |
| 4 | C | H | — |
| 5 | C | E | — |
| 6 | A | D | — |
| 7 | C | D | — |
| 8 | D | G | C |
| 9 | D | F | F |
| 10 | C | D | — |
| 12 | D | G | — |
| 13 | C | F | E |
| 14 | D | D | C |
| 15 | D | F | D |
| 19 | B | D | — |
| 26 | B | C | D |
| 27 | B | D | F |
| 28 | C | E | C |
| 29 | D | E | — |
| 31 | C | G | — |
| 32 | C | D | C |

TABLE OF BIOLOGICAL RESULTS-continued

| Compound No | Pesticidal effectiveness | | |
|---|---|---|---|
| | Spodoptera (Example 4) | Heliothis (Example 4) | Laspeyresia (Example 6) |
| 36 | D | G | — |

"—" means "not tested"

What is claimed is:

1. A compound of the formula

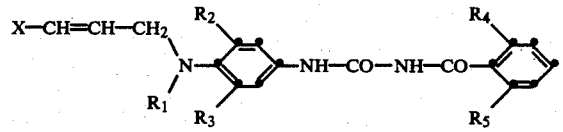

wherein $R_1$ is hydrogen, $C_1$–$C_4$-alkyl, $C_3$-alkenyl, $C_3$-alkenyl substituted by a chlorine or bromine atom, or $C_3$–$C_6$-cycloalkyl, $R_2$ and $R_3$ are each hydrogen or halogen, $R_4$ is methyl or halogen, $R_5$ is hydrogen or halogen, and X is chlorine or bromine; and salts thereof.

2. A compound according to claim 1, wherein $R_1$ is $C_1$–$C_4$-alkyl, $CH_2$=CH—$CH_2$-, Cl—CH=CH—$CH_2$—, Br—CH=CH—$CH_2$— or cyclopropyl, $R_2$ and $R_3$ are each chlorine or bromine, $R_4$ is fluorine, chlorine, bromine or methyl, and $R_5$ is hydrogen, fluorine or chlorine.

3. A compound according to claim 2, wherein $R_1$ is $C_1$–$C_4$-alkyl, and $R_4$ is fluorine or chlorine.

4. A compound according to claim 1, wherein $R_2$ and $R_3$ are chlorine.

5. A compound according to claim 1, wherein $R_1$ is methyl.

6. A compound according to claim 1, wherein $R_4$ and $R_5$ are each fluorine or chlorine.

7. A compound according to claim 6, wherein $R_4$ and $R_5$ are fluorine.

8. The compound according to claim 3 of the formula

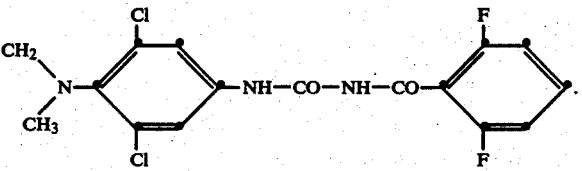

9. The compound according to claim 3 of the formula

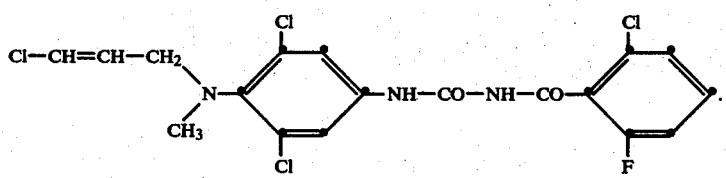

10. The compound according to claim 3 of the formula

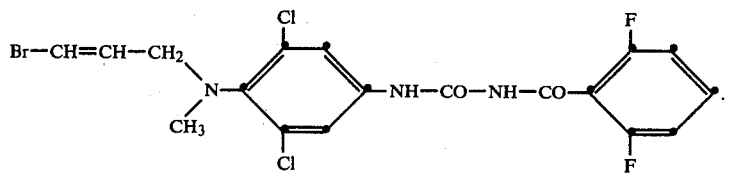

11. The compound according to claim 3 of the formula

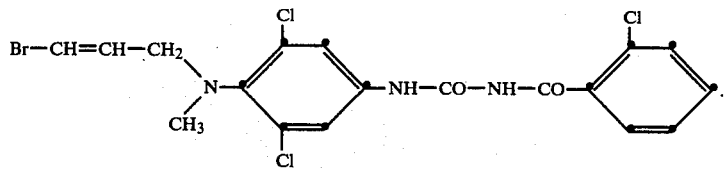

12. An insecticidal composition which contains (1) as active ingredient an insecticidally effective amount of a compound according to claim 1 and (2) a suitable carrier.

13. A method for combatting insects which comprises applying to said insects or to a locus desired to be protected from said insects an insecticidally effective amount of a compound according to claim 1.

14. A method according to claim 13 in which plant-damaging insects are combatted.